US00PP10998P

United States Patent [19]

van Rijn

[11] Patent Number: Plant 10,998

[45] Date of Patent: Jul. 6, 1999

[54] ANTHURIUM PLANT NAMED 'SUGAR LOVE'

[75] Inventor: Magdalena J. M. van Rijn, Schipluiden, Netherlands

[73] Assignee: Rijnplant B.V., Schipluiden, Netherlands

[21] Appl. No.: 09/007,032

[22] Filed: Jan. 14, 1998

[51] Int. Cl.[6] ..... A01H 5/00

[52] U.S. Cl. ..... Plt./367

[58] Field of Search ..... Plt./365, 367, 368, Plt./369

*Primary Examiner*—Lynette R. F. Smith
*Assistant Examiner*—Kent L. Bell
*Attorney, Agent, or Firm*—C. A. Whealy

[57] ABSTRACT

A distinct cultivar of Anthurium plant named 'Sugar Love', characterized by its compact, upright, outwardly arching and freely branching plant habit; dark green leaves that are cordate in shape; numerous inflorescences that are positioned above the foliage on strong and erect scapes; broad salmon-pink spathes with truncate base; and good post-production longevity.

1 Drawing Sheet

BACKGROUND OF THE INVENTION

The present invention relates to a new and distinct cultivar of Anthuriumn plant, botanically known as *Anthurium andreanum*, and hereinafter referred to by the cultivar name 'Sugar Love'.

The new Anthurium is a product of a planned breeding program conducted by the inventor in Schipluiden, The Netherlands. The objective of the program is to create new Anthurium cultivars that have a freely branching growth habit, strong plant growth, medium leaf size, rapid growth rate, strong roots, attractive spathe color, numerous inflorescences and good post-production longevity. The new cultivar originated from a cross by the inventor in 1992 of the inventor's proprietary *Anthurium andreanum* selection code number 923 as the female, or seed, parent with the inventor's proprietary *Anthurium andreanum* selection code number 9322 as the male, or pollen, parent. The cultivar 'Sugar Love' was discovered and selected by the inventor as a plant within the progeny of the stated cross in a controlled environment in Schipluiden, The Netherlands.

Asexual propagation by tissue culture of the new cultivar at Schipluiden, The Netherlands, has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of 'Sugar Love'. These characteristics in combination distinguish 'Sugar Love' as a new and distinct cultivar:

1. Compact, upright, outwardly arching and freely branching growth habit.

2. Dark green leaves that are cordate in shape.

3. Numerous inflorescences that are positioned above the foliage on strong and erect scapes.

4. Broad salmon-pink spathes with truncate base.

5. Good post-production longevity.

The new Anthurium can be compared to its female parent cultivar, the proprietary selection code number 923. Besides differing in leaf shape and spathe color, plants of the new Anthurium are different from plants of selection code number 923 in the following characteristics:

1. Plants of the cultivar 'Sugar Love' are more compact than plants of the selection code number 923.

2. Plants of the cultivar 'Sugar Love' have stronger leaves and petioles than plants of the selection code number 923.

3. Plants of the cultivar 'Sugar Love' have smaller leaves and spathes than plants of the selection code number 923.

The new Anthurium can be compared to its male parent cultivar, the proprietary selection code number 9322. Besides differing in leaf and spathe shape, plants of the new Anthurium are different from plants of selection code number 9322 in the following characteristics:

1. Plants of the cultivar 'Sugar Love' have much smaller leaves than plants of the selection code number 9322.

2. Spathe color of plants of the cultivar 'Sugar Love' is salmon-pink whereas spathe color of plants of the selection code number 9322 is orange.

The new Anthurium can be compared to the Anthurium cultivar 'Sweet Love' (U.S. Plant Patent application Ser. No. 09/007,036). Besides leaf shape, plants of the new Anthurium differ from plants of the cultivar 'Sweet Love' in the following characteristics:

1. Plants of the cultivar 'Sugar Love' are much shorter and more compact than plants of the cultivar 'Sweet Love'.

2. Plants of the cultivar 'Sugar Love' have shorter spadices and scapes than plants of the cultivar 'Sweet Love'.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical potted plant of 'Sugar Love'. Leaf and flower colors in the photographs may appear different from the actual colors due to light reflectance.

DETAILED BOTANICAL DESCRIPTION

In the following description, color references are made to The Royal Horitcultural Society Colour Chart except where general terms of ordinary dictionary significance are used. The following observations and measurements describe plants grown in Schipluiden, The Netherlands, in a glass greenhouse with an average day temperature of 25° C. and an average night temperature of 19° C.

Botanical classification: *Anthurium andreanum* cultivar 'Sugar Love'.

Parentage:

*Seed or female parent.*—Inventor's proprietary *Anthurium andreanum* selection code number 923.

*Pollen or male parent.*—Inventor's proprietary *Anthurium andreanum* selection code number 9322.

Propagation:

*Method.*—By tissue culture.

*Time to initiate roots.*—70 and 84 days at 24° C. and 21° C. temperatures, respectively.

*Rooting habit.*—Freely branching, numerous and very strong fleshy roots.

Plant Description:

*Plant shape.*—Upright, inverted triangle, symmetrical.

*Growth habit.*—Erect when young, becoming outwardly arching as leaves develop. Freely branching, bushy and dense. Appropriate for 12 to 30-cm containers.

*Plant height.*—About 60 cm from soil level to apex of spathes.

*Plant vigor.*—High.

*Growth rate.*—Moderate.

*Crop time.*—About 16 to 17 months are usually required from planting of a young plant to a finished plant.

*Stem description.*—Diameter: About 1.5 cm. Internode length: About 1 cm.

*Foliage description.*—Length: About 19 cm. Width: About 14 cm. Shape: Cordate. Apex: Apiculate. Base: Auriculate, medium lobing, not overlapping. Margin: Entire, undulating. Texture: Leathery, flexible, smooth, glabrous, somewhat glossy. Surface: Rugose, wavy. Angle with respect to petiole: Horizontal. Color: Upper surface: Darker than 137A. Lower surface: 144A/146C. Petiole: Length: About 30 cm. Diameter: Less than 4 mm. Cross-section: Rounded. Color: 144A.

Inflorescence description:

*Inflorescence arrangement.*—Spathe with spadix held above the foliage. Flowering structures arise from leaf axils. Freely flowering, numerous inflorescences per plant.

*Inflorescence longevity.*—Spathe/spadix last about six weeks under winter conditions and up to three or four months under summer conditions; inflorescences persistent.

*Flowers.*—Quantity of flowers per spadix: Numerous, about 12 flowers on the middle 2-cm portion of the spadix. Shape: Rounded. Diameter: About 1 mm.

*Spathe.*—Length: About 8.5 cm. Width: About 12 cm. Height above foliage: About 7.5 cm. Shape: Broadly cordate. Apex: Acuminate. Base: Truncate, shallow lobing, not overlapping. Margin: Entire, flat to slightly rolling inward. Texture: Leathery, glabrous, somewhat glossy. Surface; Slightly wavy. Angle with respect to scape: Perpendicular. Color: Front surface: 39B. Back surface: 41C. Margin: 143A, slightly at base of margin.

*Spadix.*—Length: About 5.5 cm. Diameter: About 9 mm. Shape: Columnar. Cross section: Rounded. Longitudinal axis: Bent before flowering. Color, just before flowering: Base: Creamy white. Apex: 14A.

*Scape.*—Length: About 40 cm. Diameter: About 5 mm. Aspect: Strong and erect. Color: Green 146A.

*Reproductive organs.*—Androecium: Pollen color: Cream white. Gynoecium: Stigma shape: Ovoid. Ovary: Protogyneous.

Disease resistance: Plants of the new Anthurium have demonstrated good tolerance to root pathogens common to Anthuriums.

Seed development: Seed development is rarely observed.

It is claimed:

1. A new and distinct cultivar of Anthurium plant named 'Sugar Love', as illustrated and described.

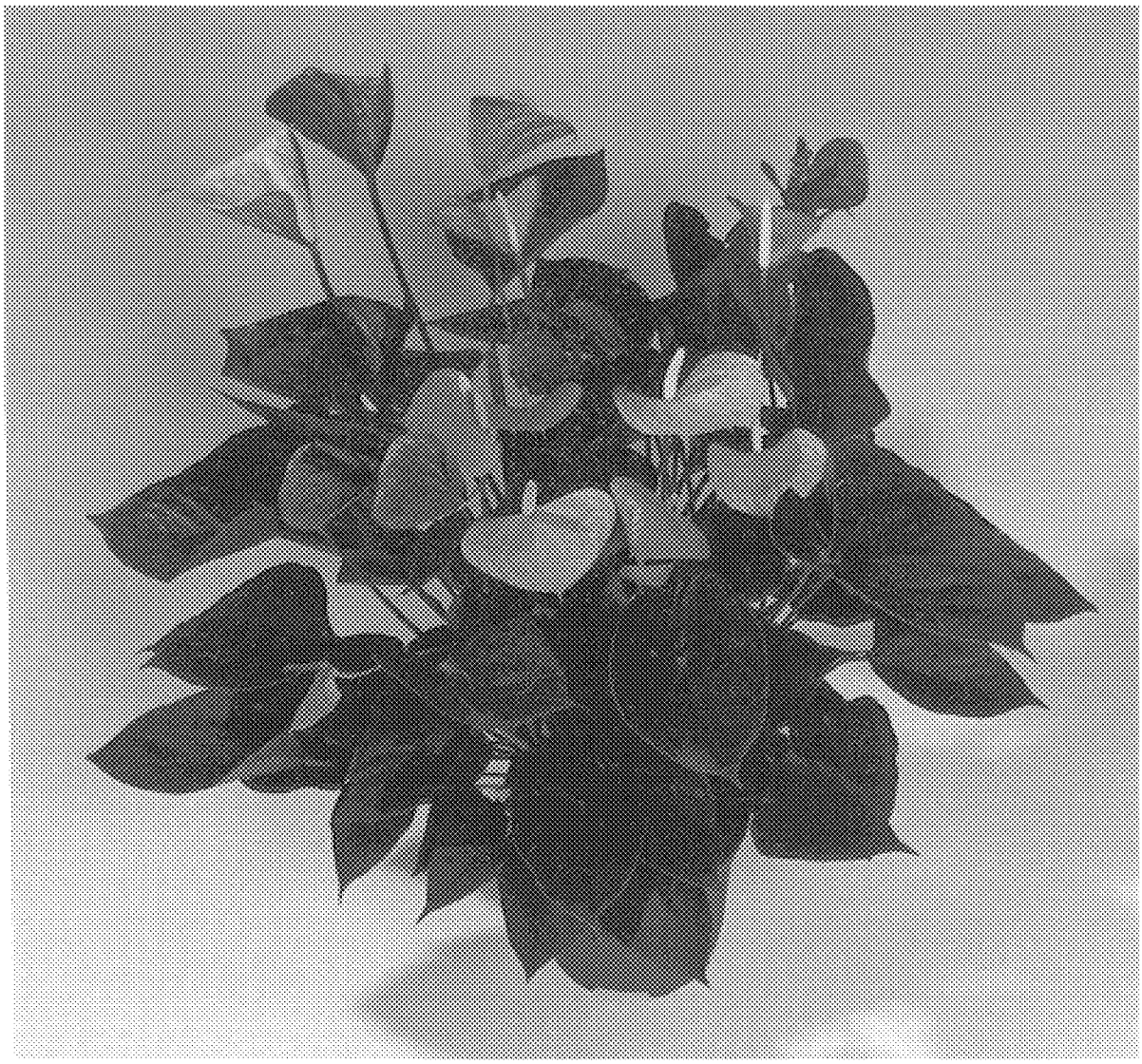

* * * * *